United States Patent [19]

Wallis et al.

[11] Patent Number: 4,880,800

[45] Date of Patent: Nov. 14, 1989

[54] AMINOCYCLOPENTYL ETHERS AND PHARMACEUTICAL FORMULATION

[75] Inventors: Christopher J. Wallis, Royton; Harry Finch, Hitchin; Peter Hallett, Royston, all of England

[73] Assignee: Glaxo Group Limited, London, England

[21] Appl. No.: 96,755

[22] Filed: Sep. 15, 1987

Related U.S. Application Data

[63] Continuation of Ser. No. 735,181, May 17, 1985, abandoned.

[30] Foreign Application Priority Data

May 18, 1984 [GB] United Kingdom ............... 8412774
Sep. 12, 1984 [GB] United Kingdom ............... 8423083

[51] Int. Cl.$^4$ .................. A61K 31/557; C07D 267/10; C07D 223/02; C07D 211/22
[52] U.S. Cl. .................................... 514/211; 514/212; 514/221; 514/227.5; 514/227.8; 514/231.5; 514/239.2; 514/255; 514/317; 514/326; 514/422; 514/428; 544/59; 544/171; 544/58.2; 544/58.7; 544/146; 544/379; 544/399; 540/596; 540/610; 546/213; 546/238; 548/527; 548/573
[58] Field of Search ............ 540/596, 610, 484; 544/59, 171, 58.2, 399, 146, 379, 58.1; 546/213, 238; 548/527, 573; 514/221, 227.5, 227.8, 231.5, 239.2, 255, 317, 326, 422, 428, 211, 212

[56] References Cited

U.S. PATENT DOCUMENTS

| | | | |
|---|---|---|---|
| 4,188,403 | 2/1980 | Orth et al. ................. | 560/43 X |
| 4,345,984 | 8/1982 | Mihelich ..................... | 204/162 |
| 4,409,213 | 10/1983 | Collington et al. ......... | 260/239 B X |
| 4,530,925 | 7/1985 | Collington et al. ......... | 260/239 B X |
| 4,613,597 | 9/1986 | Collington et al. ......... | 514/211 |

OTHER PUBLICATIONS

Topics in Current Chemistry 1977, 72 pp. 59-63 and 83-85.
J. Organic Chemistry 1983, 48, No. 4, pp. 409-417, Matthews et al.
Berger ed., Medicinal Chemistry, 3rd ed., John Wiley (1970) p.75.
Fried et al, Annals of the New York Acad. of Sci., vol. 180, (1971) pp. 38-63.

Primary Examiner—Anton H. Sutto
Assistant Examiner—Diana G. Rivers
Attorney, Agent, or Firm—Bernard, Rothwell & Brown

[57] ABSTRACT

Compounds are described of the formula

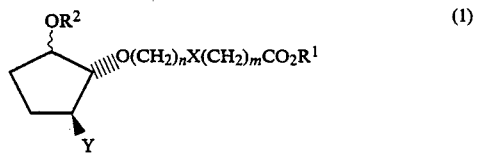

where:
$R^1$ is —H or —$CH_3$,
n is 1, m is 2-4 and X is —CH=CH— or —$CH_2CH_2$—;
Y is a saturated heterocyclic amino group,
$R^2$ is (i) substituted or unsubstituted phenylalkyl, thineylalkyl or naphthylalkyl or (ii) cinnamyl, and their salts and solvates.

These compounds inhibit blood platelet aggregation, bronchoconstriction and vasoconstriction and may be formualted for use as antithrombotic or antiasthmatic agents.

11 Claims, No Drawings

AMINOCYCLOPENTYL ETHERS AND PHARMACEUTICAL FORMULATION

This is a continuation of application Ser. No. 735,181 filed May 17, 1985 now abandoned.

The endoperoxides prostaglandins $G_2$ and $H_2$ and thromboxane $A_2$ are naturally occurring reactive metabolites of arachidonic acid in human platelets. They are not only potent aggregatory agents but are also constrictors of vascular and bronchial smooth muscle, and therefore substances which antagonise their effects are of considerable interest in human medicine.

We have now found a new group of compounds which have shown endoperoxide and thromboxane antagonist activity, and are therefore of interest in the treatment of cardiovascular diseases, asthma and adult respiratory distress syndrome and for use in renal transplant and dialysis and in the prevention of relapse of healed peptic ulcers.

The invention thus provides compounds of the general formula (I)

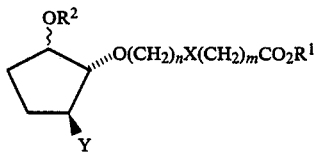
(1)

wherein:

$R^1$ is a hydrogen atom or a methyl group;

X is cis or trans —CH=CH— or —$CH_2CH_2$—, m is 2, 3 or 4 and n is 1; or X is trans —CH=CH—, m is zero and n is 3;

Y is a saturated heterocyclic amino group (attached to the cyclpentane ring via the nitrogen atom) which has 5-8 ring members and (a) optionally contains in the ring —O—, —S—, —$SO_2$—, or —$NR^3$— (where $R^3$ is a hydrogen atom, $C_{1-7}$ alkyl or aralkyl having a $C_{1-4}$ alkyl portion); and/or (b) is optionally substituted by one or more $C_{1-4}$ alkyl groups;

$R^2$ is (i) straight or branched $C_{1-5}$ alkyl substituted by (a) phenyl [optionally substituted by $C_{1-6}$ alkyl, $C_{5-7}$ cycloalkyl, phenylalkyl having a $C_{1-3}$ alkyl portion, thienyl, phenyl (optionally substituted by $C_{1-4}$ alkyl, $C_{1-4}$ alkoxy or phenyl)], (b) thienyl [optionally substituted by $C_{5-7}$ cycloalkyl or phenyl (optionally substituted by $C_{1-3}$ alkyl, $C_{1-3}$ alkoxy or halogen)], or (c) naphthyl (optionally substituted by $C_{1-4}$ alkyl or $C_{1-4}$ alkoxy) or (ii) cinnamyl;

and the physiologically acceptable salts and solvates thereof.

The structural formulae herein are to be understood to include the enantiomers of each of the compounds concerned as well as mixtures of the enantiomers including racemates, even though the precise structure as set out only relates to one enantiomer.

It will be appreciated that the invention includes compounds of formula (1a) or (1b):

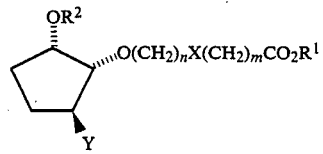
(1a)

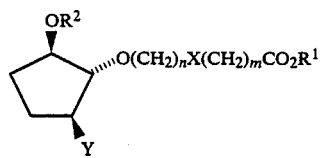
(1b)

Suitable physiologically acceptable salts of the compounds of general formula (1) include acid addition salts derived from inorganic and organic acids, such as hydrochlorides, hydrobromides, sulphates, phosphates, maleates, tartrates, citrates, 2-chlorobenzoates, p-toluenesulphonates, methane-sulphonates, salicylates, fumarates, lactates, hydroxynaphthalenecarboxylates (e.g. 1-hydroxy or 3-hydroxy-2-naphthalenecarboxylates), or furoates. When $R^1$ is —H, the compounds may also form salts with suitable bases. Examples of such salts are alkali metal (e.g. sodium and potassium), alkaline earth metal (e.g. calcium or magnesium), ammonium and substituted ammonium (e.g. dimethylammonium, triethylammonium, 2-hydroxyethyldimethylammonium, piperazine, N,N-dimethylpiperazine, piperidine, ethylenediamine and choline).

The heterocyclic amino group Y may for example have a 5, 6 or 7-membered ring, e.g. pyrrolidino, piperidino, morpholino, piperazino, thiomorpholino, 1,1-dioxothiomorpholino, homomorpholino and hexamethyleneimino. Examples of the optional substituents ($R^3$) which may be present on a second nitrogen atom in the ring are methyl, ethyl, butyl, hexyl, benzyl and phenethyl. The carbon atoms of the heterocyclic rings may for example be substituted by methyl, ethyl or butyl, and the group Y may be for example 4-methylpiperidino. Y is preferably thiomorpholino, piperidino or hexamethyleneimino, particularly piperidino or hexamethyleneimino.

In general, $R^1$ is preferably a hydrogen atom.

Where $R^2$ is a substituted alkyl group of type (i), the alkylene portion may for example contain 1-3 carbon atoms (e.g. methylene, ethylene or propylene) and is preferably a methylene or propylene group.

In $R^2$ groups of the type (i)(a), the phenyl group may be substituted by, for example, methyl, ethyl, t-butyl, cyclohexyl, thienyl, benzyl, phenethyl, or phenyl (optionally substituted by methyl, ethyl, methoxy or butoxy) groups.

In $R^2$ groups of the type (i)(b), the thienyl group may be substituted by, for example, cyclohexyl or phenyl (optionally substituted by methyl, ethyl, methoxy, ethoxy, chloro or bromo) groups.

In general $R^2$ is preferably (i) a $C_{1-5}$ alkyl (particularly methyl, ethyl or propyl) group substituted by (a) phenyl or phenyl substituted by phenyl ($C_{1-3}$) alkyl, thienyl, phenyl, $C_{1-4}$ alkylphenyl or $C_{1-4}$ alkoxyphenyl, (b) thienyl or phenylthienyl or (c) naphthyl, or (ii) cinnamyl. Thus $R^2$ may be for example (i) methyl, ethyl or propyl substituted by naphthyl, thienyl substituted by phenyl, and phenyl substituted (preferably in the para-position) by thienyl, benzyl, phenyl or phenyl substituted (preferably in the para-position) by methyl or methoxy, or (ii) cinnamyl.

Particularly preferred $R^2$ groups are benzyl substituted by phenyl or methoxyphenyl (e.g. [(1,1'-biphenyl)-4-yl]methyl or [4'-methoxy(1,1'biphenyl)-4-yl]methyl) or phenpropyl substituted by phenyl (e.g. 3-[(1,1'-biphenyl)-4-yl]propyl.

X is preferably cis or trans —CH=CH—, particularly cis —CH=CH—, when n is 1 and m is 2, 3 or 4.

When n is 1, —(CH$_2$)$_m$— is in particular —(CH$_2$)$_2$— or —(CH$_2$)$_4$—.

The preferences indicated above apply both separately and in combination with one or more of the other stated preferences.

Thus a preferred group of compounds has the formula (1) in which:

$R^1$ is a hydrogen atom;
n is 1, m is 2 and X is cis —CH=CH—;
Y is piperidino or hexamethyleneimino;
$R^2$ is benzyl substituted by phenyl or methoxyphenyl; or phenpropyl substituted by phenyl;
and the physiologically acceptable salts and solvates thereof.

In general, in compounds of formula (1a), the isomers in which the carbon atom carrying the —O(CH$_2$)$_n$X(CH$_2$)$_m$COOR$^1$ group is in the R configuration (and mixtures containing this isomer) are preferred.

Particularly preferred compounds of the invention are:

[1α(Z),2α,5β]-(±)-6-[[2-[[(1,1'-biphenyl)-4-yl]methoxy]-5-(1-piperidinyl)cyclopentyl]oxy]-4-hexenoic acid;

[1R-[1α(Z),2α,5β]]-(+)-6-[[2-[[(1,1'-biphenyl)-4-yl]methoxy]-5-(1-piperidinyl)cyclopentyl]oxy]-4-hexenoic acid;

[1α(Z),2α,5β]-(±)-6-[[2-[[(1,1'-biphenyl)-4-yl]methoxy]-5-(hexahydro-1H-azepin-1-yl)cyclopentyl]oxy]-4-hexenoic acid;

[1α(Z),2α,5β]-(±)-6-[[2-[3-[(1,1'-biphenyl)-4-yl]propoxy]-5-(1-piperidinyl)cyclopentyl]oxy]-4-hexenoic acid;

[1α(Z),2β,5β]-(±)-6-[[2-[[4'-methoxy-(1,1'-biphenyl)-4-yl]methoxy]-5-(1-piperidinyl)cyclopentyl]oxy]-4-hexenoic acid; or

[1α(Z),2β,5β]-(±)-6-[[2-[[(1,1'-biphenyl)-4-yl]methoxy]-5-(hexahydro-1H-azepin-1-yl)cyclopentyl]oxy]-4-hexenoic acid;

and the physiologically acceptable salts and solvates thereof.

Compounds of formula (1) inhibit blood platelet aggregation, bronchoconstriction and vasoconstriction. A test to determine inhibition of blood platelet aggregation is as described by G V Born (Nature 194, 927–929, (1962)) except in that collagen is used instead of ADP as the pro-aggregatory agent.

The ability of the compounds of the invention to inhibit vasoconstriction or bronchoconstriction is determined using the relevant isolated tissue (e.g. spirally cut rat aortic strip or guinea-pig lung parenchymal strip) by measuring the effect of the compound to be tested on the contraction of the tissue to [1R-[1α,4α,5β(Z),6α(-1E,3S*)]]-7-[6-(3-hydroxy-1-octenyl)-2-oxabicyclo[2,2,1]hept-5-yl]-5-heptenoic acid (U-46619).

The compounds are thus of interest in the treatment of asthma, and as inhibitors of platelet aggregation and thrombosis for use in renal transplant and dialysis and the treatment and prevention of occlusive vascular diseases such as atherosclerosis, peripheral vascular disease, cerebral vascular disease including transient ischaemic attacks, stroke, pulmonary embolism, diabetic retinopathy, post operative thrombosis, angina and myocardial infarction.

The compounds are also of potential use in the treatment of adult respiratory distress syndrome and the prevention of relapse of healed peptic ulcers.

The compounds may be formulated in a conventional manner for use with one or more pharmaceutical carriers.

For oral administration, the pharmaceutical composition may take the form of, for example, tablets, capsules, powders, solutions, syrups or suspensions prepared by conventional means with acceptable excipients.

The compounds may be formulated for parenteral administration by continuous infusion. Formulations for injections may be presented in unit dosage form in ampoules, or in multi-dose containers, with an added preservative. The compositions may take such forms as suspensions, solutions or emulsions in oil or aqueous vehicles, and may contain formulatory agents such as suspending, stabilising and/or dispersing agents. Alternatively, the active ingredient may be in powder form for reconstitution before use with a suitable vehicle e.g. sterile pyrogen-free water.

For administration by inhalation the compounds are conveniently delivered in the form of an aerosol spray presentation from pressurised packs or a nebuliser, or as a cartridge from which the powdered composition may be inhaled with the aid of a suitable device. In the case of a pressurised aerosol the dosage unit may be determined by providing a valve to deliver a metered amount.

For use as antithrombotic agents, the compounds are preferably administered orally, for example in amounts of 0.05 to 10 mg/kg body weight, 1 to 4 times daily, or intravenously, for example in amounts of 0.01 to 25 mg/kg body weight, 1 to 4 times daily.

For use in the treatment of asthma, the compounds may also be administered orally in amounts of 0.05 to 10 mg/kg body weight, 1 to 4 times daily; preferably however they are administered by inhalation at doses varying from 0.02 to 30 mg, preferably 0.02 to 3.0 mg, 1 to 4 times daily. The compounds may be used in combination with other antiasthmatic agents.

The precise dose administered will of course depend on the age and condition of the patient.

Suitable methods for preparing compounds of formula (1) are described below, the groups $R^1$, $R^2$, X and Y being as defined above except where otherwise indicated.

(a) Compounds of formula (1) in which X is —CH=CH— may be prepared by reacting an aldehyde of formula (2)

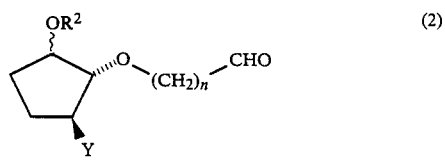

with an appropriate Wittig reagent, e.g. a phosphorane of formula $R_3^4P$=CH(CH$_2$)$_m$CO$_2$R$^1$ (where $R^4$ is $C_{1-6}$ alkyl or aryl, e.g. monocyclic aryl such as phenyl) or a salt thereof, e.g. the potassium salt. Suitable reaction solvents include hydrocarbons (e.g. benzene and toluene), ethers (e.g. tetrahydrofuran) and dialkylsulphoxides (e.g. dimethylsulphoxide). The reaction may be carried out at any suitable temperature from −70° to 70° C., for example when m is 2, 3 or 4 at room temperature.

The reaction is particularly suitable for the preparation of compounds in which $R^1$ is a hydrogen atom.

Where a compound in which n is 1 is initially formed and X is cis —CH=CH—, the configuration of X may if desired be modified (using process (e) below or X may be reduced, using process (f). $R^1$ may also be modified as desired, using processes (d) or (c).

(b) Compounds of formula (1) may be prepared by alkylation of an alkoxide (e.g. an alkali metal alkoxide) derived from an alcohol of formula (3)

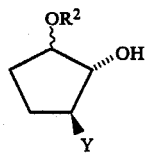
(3)

with an alkylating agent $L(CH_2)_nX(CH_2)_mCOOR^{1a}$ (where $R^{1a}$ is a carboxylic acid protecting group and L is a leaving group such as a halogen atom, e.g. a chlorine, bromine or iodine atom, or a hydrocarbylsulphonyloxy group, e.g. methanesulphonyloxy or p-toluenesulphonyloxy), and followed where necessary by removal of the protecting group. Suitable bases for the preparation of the alkoxide include for example sodium hydride. The alkoxide may be formed in a solvent (e.g. a substituted amide such as dimethylformamide) at a suitable temperature from ambient to 100° C. The alkylation agent is then added to the cooled (e.g. 0° C.) solution of the alkoxide. The protecting group may be removed by hydrolysis, for example as described in process (c) below.

In one convenient embodiment of this process the group $R^{1a}$ is tertiary butyl and the alkylation is performed using sodium hydride.

The alkylating agents $L(CH_2)_nX(CH_2)_mCOOR^{1a}$ are either known compounds or may be prepared by methods analogous to those used for the preparation of the known compounds.

(c) Compounds of formula (1) in which $R^1$ is a hydrogen atom may be prepared by hydrolysis of a corresponding ester (e.g. a $C_{1-6}$ alkyl ester such as a methyl or t-butyl ester) for example using a base such as NaOH or KOH in a suitable solvent (e.g. an alcohol such as methanol or ethanol) at a suitable temperature up to reflux.

(d) Compounds in which $R^1$ is a methyl group may be prepared by esterification of the corresponding carboxylic acid. Conventional esterification techniques may be used, for example by reaction with methanol in the presence of a mineral acid such as hydrochloric acid or sulphuric acid.

(e) Compounds of formula (1) in which X is trans —CH=CH— may be prepared by isomerising the corresponding cis compound. The isomerisation may for example by effected by treatment with p-toluene sulphinic acid in dioxan (e.g. at reflux) or azobisisobutyronitrile and thiophenol, using for example a hydrocarbon solvent (e.g. benzene) and any suitable temperature up to reflux.

(f) Compounds of formula (1) in which X is a —CH$_2$CH$_2$— group may be prepared by reduction of the corresponding compound in which X is a cis or trans —CH=CH— group. Suitable methods of reduction include hydrogen in the presence of a catalyst such as palladium, on a support (e.g. carbon). Suitable solvents include ethyl acetate, ethanol and methanol.

(g) Where salts of compounds of formula (1) are desired such salts may be formed in conventional methods, for example by treatment with an acid or with a base.

Treatment may be effected for example in a suitable solvent such as an ether (e.g. diethylether), acetonitrile, acetone, chloroform, dichloromethane, ethyl acetate, isopropyl acetate or an alcohol e.g. methanol, ethanol or isopropanol.

Salts may also be formed by conversion of one salt of a compound of the invention into another, e.g. by ion exchange using convention methods.

The intermediate aldehydes of formula (2) may be prepared from the corresponding intermediates of formula (4)

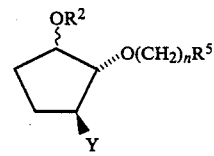
(4)

by hydrolysis of the acetal where $R^5$ is —CH(OR$^6$)$_2$ (where $R^6$ is a $C_{1-4}$ alkyl group) using for example hydrochloric acid in a solvent such as acetone or by reduction of the corresponding nitriles of formula (4) (where $R^5$ is —CN) using a suitable reducing agent (e.g. diisobutyl-aluminium hydride) in a solvent such as dichloromethane at a suitable temperature (e.g. −78° C.).

An acetal or nitrile of formula (4) may be prepared by alkylation of a corresponding alcohol of formula (3) using an alkylating agent $L(CH_2)_nR^5$ as described in process (b) above.

The intermediate alcohols of formula (3) may be prepared from the epoxy-ethers of formula (5)

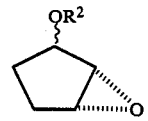
(5)

by reaction with an amine YH in a solvent such as butanol at a suitable temperature up to reflux.

The epoxy-ethers of formula (5) may be prepared by epoxidation of the ethers of formula (6)

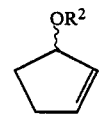
(6)

using a per-acid such as m-chloroperbenzoic acid in a solvent such as dichloromethane. The ether of formula (6) may be obtained by alkylation of the alcohol of formula (7)

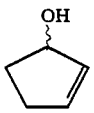

(7)

with a compound R²L under the conditions described for process (b) above.

Alternatively, the epoxy-ethers of formula (5) in which —OR² is in the α-position may be prepared by alkylation of the alcohol of formula (8)

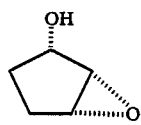

(8)

with a compound R²L under the conditions described in process (b) above.

The alcohol of formula (8) may be obtained from the alcohol of formula (7) as described by T. Itoh et al. in J. Amer. Chem. Soc., 1979, 101, 159.

When a specific enantiomer of formula (1) is required, starting materials having the desired stereochemical configuration should be used in the above processes. For example, individual enantiomers of the alcohol of formula (7) may be obtained from the corresponding racemic alcohol, using methods such as those described by V. S. Martin et al. in J. Amer. Chem. Soc., 1981, 103, 6237. Alternatively, the enantiomers of an alcohol of formula (3) may be prepared using for example a suitable chiral resolving agent such as resolved 1-(1-naphthyl)ethyl isocyanate as described in the Examples below and as described by W. H. Pirkle and M. S. Hoekstra in J. Org. Chem., 1974, 39, 3904.

The following examples illustrate the invention.
Temperatures are in °C.
Chromatography and thin layer chromatography (t.l.c.) was carried out using the following systems:
(A) Silica
(B) Triethylamine deactivated silica
(C) Neutral alumina (activity 2 for column chromatography)
Dried refers to drying with MgSO₄.
NaH refers to a dispersion of sodium hydride in oil.
The following abbreviations are used.
EA—ethyl acetate
ER—diethyl ether
DMF—dimethylformamide
THF—tetrahydrofuran
PE—petroleum ether (b.p. 40°–60°)

INTERMEDIATE 1

(1a)

(1α,2β,5α)-(±)-2-[[(1,1'-Biphenyl)-4-yl]methoxy]-6-oxabicyclo-[3.1.0]hexane

NaH (0.44 g; 60%) was added to a cold (0°), stirred solution of (1α,2β,5α)-(±)-6-Oxabicyclo[3.1.0]hexan-2-ol (1 g) and 4-(bromomethyl)-(1,1'-biphenyl) (2.72 g) in dry DMF (6 ml). After 1 h the suspension was poured into brine (100 ml) and extracted with ER (3×50 ml). The combined extracts were dried and evaporated and the residue was purified by chromatography (A) using 3:2 PE-ER as eluant to give the title compound as a solid (2.44 g) m.p. 65°–67°.

The following compounds were prepared in a similar manner:

(1b) (1α,2β,5α)-(±)-2-[4-(Phenylmethyl)phenylmethoxy]-6-oxabicyclo[3.1.0]hexane, m.p. 38°–42° using 1-(bromomethyl)-4-(phenylmethyl)-benzene. Purification by chromatography (A) using 2:1, followed by 3:2, PE-ER as eluant.

(1c) (1α,2β,5α)-(±)-2-[(5-Phenyl-3-thienyl)methoxy]-6-oxabicyclo[3.1.0]hexane, m.p. 38°–40° using 4-(bromomethyl)-2-phenylthiophene. Purification by chromatography (A) using initially CH₂Cl₂ followed by 3:1 CH₂Cl₂-ER as eluant.

(1d) (±)-4-[[2-Cyclopenten-1-yloxy]methyl](1,1'-biphenyl), from 2-cyclopentenol and 4-(bromomethyl)(1,1'-biphenyl). Purification by chromatography (A) using 19:1 PE-ER as eluant.

Analysis. Found: C, 86.6; H, 7.4. C₁₈H₁₈O requires C, 86.4; H, 7.3%.

(1e) (±)-4-[3-[2-Cyclopenten-1-yloxy]propyl](1,1'-biphenyl), from 2-cyclopentenol and 3-[(1,1'-biphenyl)-4-yl]propanol 4-methylbenzenesulphonate using 80% NaH. Purification by chromatography (A) using 19:1 PE-ER as eluant.

Analysis. Found: C, 86.3; H, 8.1. C₂₀H₂₂O requires C, 86.3; H, 8.0%.

(1f) (±)-4-[[2-Cyclopenten-1-yloxy]methyl]-4'-methoxy(1,1'-biphenyl), m.p. 54°–50° from 2-cyclopentenol and 4-(bromomethyl)-4'-methoxy(1,1'-biphenyl) using 80% NaH. Purification by chromatography (A) using 5:1 PE-ER as eluant.

INTERMEDIATE 2

(2a) (1α,2α,5α)-(±)-2-[[(1,1'-Biphenyl)-4-yl]methoxy]-6-oxabicyclo[3.1.0]hexane m-Chloroperoxybenzoic acid (85%, 812 mg) was added over 1.5 h to a cold (0°) stirred solution of Intermediate 1d (1 g) in CH₂Cl₂ (30 ml). After 20 h at ambient temperature the mixture was filtered and the filtrate washed with a solution of K₂CO₃ (5 g) and Na₂SO₃ (1 g) in water (20 ml). The aqueous layer was extracted with CH₂Cl₂ (2×25 ml) and the combined organic layers were dried and evaporated. The residue was purified by chromatography (A) using 3:1 PE-ER as eluant to give the title compound as an oil (653 mg).

Analysis. Found: C, 81.5; H, 7.2. C₁₈H₁₈O₂ requires C, 81.2; H, 6.8%.

Further elution of the column using 3:1 PE-ER gave an isomeric compound (370 mg) identical with the product of Intermediate 1a.

The following compounds were prepared in a similar manner:

(2b) (1α,2α,5α)-(±)-2-[3-[(1,1'-Biphenyl)-4-yl]propoxy]-6-oxabicyclo[3.1.0]hexane, from Intermediate 1e. Purification by chromatography (A) using 3:1 PE-ER as eluant.

Analysis. Found: C, 81.8; H, 7.6. C₂₀H₂₂O₂ requires C, 81.6; H, 7.5%.

Further elution of the column using 3:1 PE-ER gave the isomeric compound:

(2c) (1α,2β,5α)-(±)-2-[3-[(1,1'-Biphenyl)-4-yl]propoxy]-6-oxabicyclo[3.1.0]hexane, m.p. 40°–41°.

(2d) (1α,2α,5α)-(±)-2-[[4'-Methoxy-(1,1'-biphenyl)-4-yl]methoxy]-6-oxabicyclo[3.1.0]hexane, m.p. 78.5°–80.5° from Intermediate 1f. Purification by chromatography (A) using 3:1 PE-ER as eluant.

Further elution of the column using 3:1 PE-ER gave the isomeric compound:

(2e) (1α,2β,5α)-(±)-2-[[4'-Methoxy-(1,1'-biphenyl)-4-yl]methoxy]-6-oxabicyclo[3.1.0]hexane, m.p. 77°-78.5°.

INTERMEDIATE 3

(3a) (1α,2α,5β)-(±)-2-[[(1,1'-Biphenyl)-4-yl]methoxy]-5-(1-piperidinyl)cyclopentanol A solution of Intermediate 1a (1.35 g) and piperidine (6 ml) in butan-1-ol (18 ml) was heated under reflux for 24 h. The solvent and the excess piperidine were removed in vacuo and the residue was crystallised from ER to give the title compound (1.05 g) m.p. 47°-48°. The following compounds were prepared in a similar manner:

(3b) (1α,2α,5β)-(±)-2-(Phenylmethoxy)-5-(1-piperidinyl)cyclopentanol, from (1α,2β,5α)-(±)-2-(Phenylmethoxy)-6-oxabicyclo[3.1.0]hexane and piperidine. Purification by chromatography (A) using 4:1 EA-methanol as eluant.

Analysis. Found: C, 74.4; H, 9.2; N, 5.3. $C_{17}H_{25}NO_2$ requires C, 74.1; H, 9.15; N, 5.1%.

(3c) (1α,2α,5β)-(±)-2-[3-[(1,1'-Biphenyl)-4-yl]propoxy]-5-(1-piperidinyl)cyclopentanol, m.p. 27°-29° from Intermediate 2c and piperidine. Purification by chromatography (C) using EA as eluant.

(3d) (1α,2α,5β)-(±)-2-[[4'-Methoxy-(1,1'-biphenyl)-4-yl]methoxy]-5-(1-piperidinyl)cyclopentanol, from Intermediate 2e and piperidine. Purification by chromatography (A) using 89:10:1 EA-methanol-Et$_2$N as eluant.

Analysis. Found: C, 75.8; H, 8.7; N, 3.7. $C_{24}H_{31}NO_2$ requires C, 75.6; H, 8.2; N, 3.7%.

(3e) (1α,2α,5β)-(±)-2-[4-(Phenylmethyl)phenylmethoxy]-5-(1-piperidinyl)cyclopentanol, from Intermediate 1b and piperidine. Purification by chromatography (A) using 100:5:2, followed by 90:10:2, EA-methanol-Et$_3$N as eluant.

Analysis. Found: C, 78.6; H, 8.55; N, 3.9. $C_{24}H_{31}NO_2$ requires C, 78.9; H, 8.55; N, 3.8%.

(3f) (1α,2α,5β)-(±)-2-[(5-Phenyl-3-thienyl)methoxy]-5-(1-piperidinyl)cyclopentanol, m.p. 106°-108° from Intermediate 1c and piperidine. Purification by crystallisation from EA.

(3g) (1α,2α,5β)-(±)-2-[[(1,1'-Biphenyl)-4-yl]methoxy]-5-(4-morpholinyl)cyclopentanol, m.p. 97°-98.5° C. from Intermediate 1a and morpholine. Purification initially by chromatography (C) using ER as eluant and then by crystallisation from ER.

(3h) (1α,2α,5β)-(±)-2-[[(1,1'-Biphenyl)-4-yl]methoxy]-5-(hexahydro-1H-azepin-1-yl)cyclopentanol, from Intermediate 1a and hexahydro-1H-azepine. Purification by chromatography (C) using EA as eluant.

I.r. (CHBr$_3$) 3540 cm$^{-1}$.

(3i) (1α,2α, 5β)-(±)-2-[[(1,1'-Biphenyl)-4-yl]methoxy]-5-(1-pyrrolidinyl)cyclopentanol, from Intermediate 1a and pyrrolidine. Purification by chromatography (C) using 2:1 EA-ER as eluant.

Analysis. Found: C, 78.0; H, 8.5; N, 4.2. $C_{22}H_{27}NO_2$ requires C, 78.3; H, 8.1; N, 4.15%.

(3j) (1α,2α,5β)-(±)-2-[[(1,1'-Biphenyl)-4-yl]methoxy]-5-(4-thiomorpholinyl)cyclopentanol, m.p. 76°-80° from Intermediate 1a and thiomorpholine. Purification initially by chromatography (A) using 95:5:2 EA-methanol-Et$_3$N as eluant and then by crystallisation from PE-isopropyl acetate.

(3k) (1α,2β,5β)-(±)-2-[[(1,1'-Biphenyl)-4-yl]methoxy]-5-(1-piperidinyl)cyclopentanol, m.p. 89°-90° from Intermediate 2a and piperidine. Purification by chromatography (C) using 1:1 EA-ER as eluant.

(3l) (1α,2β,5β)-(±)-2-[[(1,1'-Biphenyl)-4-yl]methoxy]-5-(hexahydro-1H-azepin-1-yl)cyclopentanol, m.p. 62°-63° from Intermediate 2a and hexahydro-1H-azepine. Purification by chromatography (C) using EA as eluant.

(3m) (1α,2β,5β)-(±)-2-[3-[(1,1'-Biphenyl)-4-yl]propoxy]-5-(1-piperidinyl)cyclopentanol, m.p. 47°-48° from Intermediate 2b and piperidine. Purification by chromatography (C) using EA as eluant.

(3n) (1α,2β,5β)-(±)-2-[[4'-Methoxy-(1,1'-biphenyl)-4-yl]methoxy]-5-(1-piperidinyl)cyclopentanol, m.p. 55°-59° from Intermediate 2d and piperidine. Purification by chromatography (A) using 89:10:1 EA-methanol-Et$_3$N as eluant.

INTERMEDIATE 4

(4a) (1α,2β,3β)-(±)-1-[3-[[(1,1'-Biphenyl)-4-yl]methoxy]-2-[(2,2-dimethoxy)ethoxy]cyclopentyl]piperidine NaH (165 mg; 60%) was added under N$_2$ to a stirred solution of bromoacetaldehyde dimethylacetal (0.49 ml) and Intermediate 3a (0.8 g) in dry DMF (8 ml). After 20 h the suspension was poured into brine (150 ml) and extracted with EA (3×50 ml). The combined extracts were dried and evaporated and the residue was purified by chromatography (C) using 1:1 EA-ER as eluant to give the title compound as a solid (0.6 g) m.p. 35°-36°.

The following compounds were prepared in a similar manner:

(4b) (1α,2β,3α)-(±)-1-[3-[[(1,1'-Biphenyl)-4-yl]methoxy]-2-[(2,2-dimethoxy)ethoxy]cyclopentyl]piperidine, from Intermediate 3k. Purification by chromatography (C) using 1:1 PE-ER as eluant.

T.l.c. (C) 1:1 PE-ER Rf 0.29

(4c) (1α,2α,5β)-(±)-4-[2-[[(1,1'-Biphenyl)-4-yl]methoxy]-5-(1-piperidinyl)cyclopentyl]oxy]butanenitrile, from Intermediate 3a and 4-bromobutyronitrile. Purification initially by chromatography (A) using 95:4:1 CH$_2$Cl$_2$-methanol-Et$_3$N as eluant followed by chromatography (C) using 9:1 ER-EA as eluant.

I.r. (CHBr$_3$) 2240 cm$^{-1}$.

INTERMEDIATE 5

(5a) (1α,2α,5β)-(±)-[2-[[(1,1'-Biphenyl)-4-yl]methoxy]-5-(1-piperidinyl)cyclopentyl]oxy]ethanal Conc. hydrochloric acid (3 ml) was added slowly to a stirred solution of Intermediate 4a (0.56 g) in acetone (20 ml) and water (6 ml). After 3 h a solution of K$_2$CO$_3$ (3 g) in water (20 ml) was added at 0°. The solution was diluted with pH 6.5 phosphate buffer (150 ml) and extracted with CH$_2$Cl$_2$ (3×50 ml). The combined extracts were dried and evaporated to give the title compound as a gum (0.5 g).

I.r. (CHBr$_3$) 1733 cm$^{-1}$.

The following compound was prepared in a similar manner:

(5b) (1α,2β,5β)-(±)-[2-[[(1,1'-Biphenyl)-4-yl]methoxy]-5-(1-piperidinyl)cyclopentyl]oxy]ethanal, from Intermediate 4b.

T.l.c. (A) 1:1:0.01 EA-methanol-Et$_3$N Rf 0.62.

INTERMEDIATE 6

(1α,2α,5β)-(±)-4-[[2-[[(1,1'-Biphenyl)-4-yl]methoxy]-5-(1-piperidinyl)cyclopentyl]oxy]butanal Diisobutylaluminium hydride (1.44 ml, 1M in hexane) was added dropwise under nitrogen to a cold (−78°) stirred solution of Intermediate 4c (200 mg) in CH$_2$Cl$_2$ (15 ml). The mixture was allowed to warm to ambient temperature and stirred for 2 h. Methanol (2 ml) was added and the mixture was poured into 2N H₂SO₄ (50 ml). The suspension was adjusted to pH 8–9 using 2H NaOH solution and extracted with CH₂Cl₂ (3×50 ml). The combined extracts were dried and evaporated to give the title compound as an oil (200 mg).

T.l.c. (C) 9:1 ER-EA Rf 0.28.

INTERMEDIATE 7

(7a) [1R-[1α(R*),2α,5β]]-(+)-2-[[(1,1'-Biphenyl)-4-yl]methoxy]-5-(1-piperidinyl)cyclopentyl]-1-(1-naphthalenyl)ethylcarbamate A mixture of Intermediate 3a (3.28 g) and R-(−)-1-(1-naphthyl)ethyl isocyanate (2.78 g) in 9:1 toluene-Et₃N was heated at 100° in a sealed vessel for 20 h. Most of the solvent was removed in vacuo and the residue was purified by repeated chromatography (B) using 4:1 CH₂Cl₂-EA as eluant. The faster running (t.l.c.) diastereomer was crystallised from CH₂Cl₂-ER-PE at 0° to give the title compound (0.6 g). A portion was recrystallised from EA-methanol m.p. 131°–135°

$[\alpha]_D^{20} = +19.7°$ (CHCl₃)

N.m.r. (CDCl₃) δ2.86 (CHN); δ4.0 (CHOCH₂).

Further elution of the column gave the slower running diastereomer which was further purified by chromatography (C) using 9:1 CH₂Cl₂-EA as eluant and crystallisation from EA to give:

(7b) [1S-[1α(S*),2α,5β]]-(−)-2-[[(1,1'-Biphenyl)-4-yl]methoxy]-5-(1-piperidinyl)cyclopentyl]-1-(1-naphthalenyl)ethylcarbamate, (850 mg).

m.p. 148°–150°, $[\alpha]_D^{21.2} = -11.7°$ (CHCl₃)

N.m.r. (CDCl₃) δ2.96 (CHN); δ3.95(CHOCH₂)

The following compounds were prepared in a similar manner:

(7c) [1R-[1α(R*),2β,5β]]-(+)-[2-[[(1,1'-Biphenyl)-4-yl]methoxy]-5-(1-piperidinyl)cyclopentyl]-1-(1-naphthalenyl)ethylcarbamate, from Intermediate 3k. Purification by chromatography (A) using 9:1 CH₂Cl₂-ER followed by gradient elution up to 1:1 CH₂Cl₂-ER. The faster running diastereomer was re-chromatographed (B) using 5:1 CH₂Cl₂-ER as eluant to give the title compound as a foam.

$[\alpha]_D^{23} = +11.3°$ (CHCl₃)

T.l.c. (C) 5:1 CH₂Cl₂-ER Rf 0.5

N.m.r. (CDCl₃) δ2.77 (CHN); δ3.82 (CHOCH₂)

The slower running diastereomer was re-chromatographed (B) using 5:1 CH₂Cl₂-ER as eluant to give (7d) [1S-[1α(S*),2β,5β]]-(+)-[2-[[(1,1'-Biphenyl)-4-yl]methoxy]-5-(1-piperidinyl)cyclopentyl]-1-(1-naphthalenyl)ethylcarbamate T.l.c. (C) 5:1 CH₂Cl₂-ER Rf 0.3

$[\alpha]_D^{24} = +8.4°$ (CHCl₃)

N.m.r. (CDCl₃) δ2.8 (CHN); δ3.72 (CHOCH₂)

INTERMEDIATE 8

(8a) [1R-(1α,2α,5β)]-(+)-2-[[(1,1'-Biphenyl)-4-yl]methoxy]-5-(1-piperidinyl)cyclopentanol A solution of Intermediate 7a (0.8 g) in CH₂Cl₂ (11 ml) was treated with Et₃N (374 mg) and Cl₃SiH (498 mg) and the mixture was stirred at 20° for 2 h. The mixture was diluted with CH₂Cl₂ (50 ml) and pH 6.5 phosphate buffer (50 ml) and stirred for 18 h. The solids were removed by filtration and washed well with CH₂Cl₂ and buffer. The combined organic layers were dried and evaporated and the residue was purified by chromatography (B) using EA followed by 9:1 EA-methanol as eluant. The resulting product in CH₂Cl₂ (50 ml) was washed with pH 6.5 phosphate buffer (2×25 ml) and the organic layer was dried and evaporated to give the title compound as a solid m.p. 84°–86°.

$[\alpha]_D^{23} = +37°$ (CHCl₃)

The following compounds were prepared in a similar manner:

(8b) [1S-(1α,2α,5β)]-(−)-2-[[(1,1'-Biphenyl)-4-yl]methoxy]-5-(1-piperidinyl)cyclopentanol, m.p. 86°–88° from Intermediate 7b.

$[\alpha]_D^{25} = -34°$ (CHCl₃)

(8c) [1R-(1α,2β,5β)]-(+)-2-[[(1,1'-Biphenyl)-4-yl]methoxy]-5-(1-piperidinyl)cyclopentanol, m.p. 103°–104° from Intermediate 7c.

$[\alpha]_D^{21.7} = +8.9°$ (CHCl₃)

(8d) [1S-(1α,2β,5β)]-(−)-2-[[(1,1,'-Biphenyl)-4-yl]methoxy]-5-(1-piperidinyl)cyclopentanol, m.p. 99°–101° from Intermediate 7d.

$[\alpha]_D^{23} = -9.8°$ (CHCl₃)

INTERMEDIATE 9

(9a) [1R-[1α(Z),2α,5β]]-(+)-1,1-Dimethylethyl 6-[[2-[[(1,1'-Biphenyl)-4-yl]methoxy]-5-(1-piperidinyl)cyclopentyl]oxy]-4-hexenoate A solution of Intermediate 8a (416 mg) in dry DMF (4 ml) containing NaH (70 mg, 80%) was stirred under nitrogen and heated to complete hydrogen evolution. The cooled (0°) mixture was treated with Intermediate 10 (0.47 ml) and after 30 min. the cooling bath was removed and the mixture was stirred at ambient temperature for 1.5 h. The mixture was cautiously added to pH 6.5 phosphate buffer (75 ml) and extracted with EA (3×60 ml). The combined extracts were dried and evaporated and the residue was purified by chromatography (B) using EA as eluant to give the title compound as an oil (461 mg).

I.r. (CHBr₃) 1720 cm⁻¹

$[\alpha]_D^{23.1} = +52.6°$ (CHCl₃)

The following compounds were prepared in a similar manner:

(9b) [1R-[1α(Z),2α,5β]]-(−)-1,1-Dimethylethyl 6-[[2-[[(1,1'-Biphenyl)-4-yl]methoxy]-5-(1-piperidinyl)cyclopentyl]oxy]-4-hexenoate, from Intermediate 8b. Purification by chromatography (B) using EA as eluant.

I.r. (CHBr₃) 1720 cm⁻¹

$[\alpha]_D^{21.3} = -52.8°$ (CHCl₃)

(9c) [1α(Z),2α,5β]-(±)-1,1-Dimethylethyl 6[[2-(Phenylmethoxy)-5-(1-piperidinyl)cyclopentyl]oxy]-4-hexenoate, from Intermediate 3b. Purification by chromatography (C) using 9:1 CH₂Cl₂-ER as eluant.

Analysis. Found: C, 72.9; H, 9.0; N, 3.4. C₂₇H₄₁NO₄ requires C, 73.1; H, 9.3; N, 3.2%.

(9d) [1α(Z),2α,5β]-(±)-1,1-Dimethylethyl 6-[[2-[3-[(1,1'-Biphenyl)-4-yl]propoxy]-5-(1-piperidinyl)cyclopentyl]oxy]-4-hexenoate, from Intermediate 3c. Purification by chromatography (B) using ER as eluant.

I.r. (CHBr₃) 1720 cm⁻¹

(9e) [1α(Z),2α,5β]-(±)-1,1-Dimethylethyl 6-[[2-[[4'-Methoxy-(1,1'-biphenyl)-4-yl]methoxy]-5-(1-piperidinyl)cyclopentyl]oxy]-4-hexenoate, from Intermediate 3d. Purification by chromatography (C) using 1:1 ER-PE as eluant.

Analysis. Found: C, 74.4; H, 8.95; N, 2.5. C₃₄H₄₇NO₄ requires C, 74.3; H, 8.6; N, 2.55%.

(9f) [1α(Z),2α,5β]-(±)-1,1-Dimethylethyl 6-[[2-[4-(Phenylmethyl)phenylmethoxy]-5-(1-piperidinyl)cyclopentyl]oxy]-4-hexenoate, from Intermediate 3e. Purification by chromatography (A) using 50:25:1 ER-CH₂Cl₂-Et₃N as eluant.

I.r. (CHBr$_3$) 1720 cm$^{-1}$ (9g) [1α(Z),2α,5β]-(±)-1,1-Dimethylethyl 6-[[2-[(5-Phenyl-3-thienyl)methoxy]-5-(1-piperidinyl)cyclopentyl]oxy]-4-hexenoate, from Intermediate 3f. Purification by chromatography (B) using ER followed by 49:1 methanol-ER as eluant.

Analysis. Found: C, 70.3; H, 8.4; N, 2.7. C$_{31}$H$_{43}$NO$_4$S requires C, 70.8; H, 8.2; N, 2.7%.

(9h) [1α(Z),2α,5β]-(±)-1,1-Dimethylethyl 6-[[2-[[(1,1'-Biphenyl)-4-yl]methoxy]-5-(4-morpholinyl)cyclopentyl]oxy]-4-hexenoate, from Intermediate 3g. Purification by chromatography (C) using CH$_2$Cl$_2$ followed by 19:1 CH$_2$Cl$_2$-ER as eluant.

Analysis. Found: C, 74.05; H, 8.0; N, 3.2. C$_{32}$H$_{43}$NO$_5$ requires C, 73.7; H, 8.3; N, 2.7%.

(9i) [1α(Z),2α,5β]-(±)-1,1-Dimethylethyl 6-[[2-[[(1,1'-Biphenyl)-4-yl]methoxy]-5-(hexahydro-1H-azepin-1-yl)cyclopentyl]oxy]-4-hexenoate, from Intermediate 3h. Purification by chromatography (B) using ER as eluant.

Analysis. Found: C, 76.25; H, 9.05; N, 2.9. C$_{34}$H$_{47}$NO$_4$ requires C, 76.5; H, 8.9; N, 2.6%.

(9j) [1α(Z),2α,5β]-(±)-1,1-Dimethylethyl 6-[[2-[[(1,1'-Biphenyl)-4-yl]methoxy]-5-(1-pyrrolidinyl)cyclopentyl]oxy]-4-hexenoate, from Intermediate 3i. Purification by chromatography (A) using 95:5:2 EA-methanol-Et$_3$N as eluant.

Analysis. Found: C, 75.6; H, 9.1; N, 3.0. C$_{32}$H$_{43}$NO$_4$ requires C, 76.0; H, 8.6; N,2.8%.

(9k) [1α(Z),2α,5β]-(±)-1,1-Dimethylethyl 6-[[2-[[(1,1'-Biphenyl)-4-yl]methoxy-5-(4-thiomorpholinyl)cyclopentyl]oxy]-4-hexenoate, from Intermediate 3j. Purification by chromatography (A) using 100:1:2 EA-methanol-Et$_3$N as eluant followed by chromatography (C) using 1:1 PE-ER as eluant.

Analysis. Found: C, 71.7; H, 8.4; N, 2.6. C$_{32}$H$_{43}$NO$_4$S requires C, 71.5; H, 8.1; N, 2.6%.

(9l) (1α,2α,5β)-(±)-1,1'-Dimethylethyl 6-[[2-[[(1,1'-Biphenyl)-4-yl]methoxy]-5-(1-piperidinyl)cyclopentyl]oxy]hexanoate, from Intermediate 3a and 1,1-dimethylethyl 6-iodohexanoate. Purification by chromatography (C) using ER as eluant.

Analysis. Found: C, 75.8; H, 9.4; N, 2.8. C$_{33}$H$_{47}$NO$_4$ requires C, 76.0; H, 9.1; N, 2.7%.

(9m) (1α,2α,5β)-(±)-1,1-Dimethylethyl 7-[[2-[[(1,1'-Biphenyl)-4-yl]-methoxy]-5-(1-piperidinyl)cyclopentyl]oxy]heptanoate, from Intermediate 3a and 1,1-dimethylethyl 7-iodoheptanoate. Purification by chromatography (C) using 4:1 ER-PE as eluant.

Analysis. Found C, 76.0; H, 9.1; N, 2.6. C$_{34}$H$_{49}$NO$_4$ requires C, 76.2; H, 9.2; N, 2.6%.

(9n) [1α(Z),2β,5β]-(±)-1,1-Dimethylethyl 6-[[2-[[(1,1'-Biphenyl)-4-yl]methoxy]-5-(hexahydro-1H-azepin-1-yl)cyclopentyl]oxy]-4-hexenoate, from Intermediate 3l. Purification by chromatography (B) using ER as eluant.

I.r. (CHBr$_3$) 1720 cm$^{-1}$.

(9o) [1R-[1α(Z),2β,5β]]-(+)-1,1-Dimethylethyl 6-[[2-[[(1,1'-Biphenyl)-4-yl]methoxy]-5-(1-piperidinyl)cyclopentyl]oxy]-4-hexenoate, from Intermediate 8c. Purification by chromatography (B) using EA as eluant.

Analysis. Found: C, 76.3; H, 9.0; N, 2.9. C$_{33}$H$_{45}$NO$_4$ requires C, 76.3; H, 8.7; N, 2.7%.

$[\alpha]_D^{20.7} = +1.9°$ (CHCl$_3$)

(9p) [1S-[1α(Z),2β,5β]]-(−)-1,1-Dimethylethyl 6-[[2-[[(1,1'-Biphenyl)-4-yl]methoxy]-5-(1-piperidinyl)cyclopentyl]oxy]-4-hexenoate, from Intermediate 8d. Purification by chromatography (B) using ER as eluant.

Analysis. Found: C, 76.45; H, 9.1; N, 2.6. C$_{33}$H$_{45}$NO$_4$ requires C, 76.3; H, 8.7; N, 2.7%.

$[\alpha]_D^{19.5} = -1.1°$ (CHCl$_3$)

(9q) [1α(Z),2β,5β]-(±)-1,1-Dimethylethyl 6-[[2-[3-[(1,1'-Biphenyl)-4-yl]propoxy]-5-(1-piperidinyl)cyclopentyl]oxy]-4-hexenoate, from Intermediate 3m. Purification by chromatography (B) using ER as eluant.

I.r. (CHBr$_3$) 1720 cm$^{-1}$.

(9r) [1α(Z),2β,5β]-(±)-Dimethylethyl 6-[[2-[[4'-Methoxy-(1,1'-biphenyl)-4-yl]methoxy]-5-(1-piperidinyl)cyclopentyl]oxy]-4-hexenoate, from Intermediate 3n. Purification by chromatography (C) using 1:1 ER-PE as eluant.

Analysis. Found: C, 73.8; H, 8.5; N, 2.5. C$_{34}$H$_{47}$NO$_5$ requires C, 74.3; H, 8.6; N, 2.55%.

INTERMEDIATE 10

Z-1,1-Dimethylethyl 6-Chloro-4-hexenoate n-BuLi (1.6M, 6 ml) was added over 5 min. to a stirred, cooled (−10°) solution of cyclohexylisopropylamine (1.64 ml) in dry THF (10 ml) under nitrogen. After 5 min., the solution was cooled to −78° and 15 min. later tert-butyl acetate (1.35 ml) was added over 5 min. After 20 min. cis-1,4-dichloro-2-butene (4 ml) was added and the mixture was allowed to warm to 10° over 4 h. The mixture was diluted with 1N HCl (25 ml) and extracted with ER (2×30 ml). The combined extracts were successively washed with 1N HCl (20 ml), brine (20 ml) and 8% NaHCO$_3$ solution (20 ml) then dried and evaporated. The excess of dichloromethane was removed in vacuo and the residue was purified by chromatography (A) using PE, followed by 1:1 CH$_2$Cl$_2$-PE increasing to CH$_2$Cl$_2$ as eluant to give the title compound as an oil (0.66 g)

Analysis. Found: C, 58.6; H, 8.3. C$_{10}$H$_{17}$ClO$_2$ requires C, 58.7; H, 8.4%.

EXAMPLE 1

[1α(Z),2α,5β]-(±)-6-[[2-[[(1,1'-Biphenyl)-4-yl]methoxy]-5-(1-piperidinyl)cyclopentyl]oxy]-4-hexenoic acid, hydrochloride 3-Carboxypropyltriphenylphosphonium bromide (1.64 g) was added to a stirred solution of potassium tert-butoxide (0.86 g) in dry THF (30 ml) under N$_2$. After 15 min a solution of Intermediate 5a (0.5 g) in dry THF (15 ml) was added and stirring continued for 0.5 h. Water (5 ml) was added and the solvent removed in vacuo. The residue in water (50 ml) was washed with ER (2×30 ml; discarded) and then adjusted to pH 6.5 using dilute hydrochloric acid. The aqueous solution was extracted with CH$_2$Cl$_2$ (3×50 ml) and the combined extracts were dried and evaporated. The residue was purified by chromatography (A) using 1:1:0.01 EA-methanol-Et$_3$N as eluent to give an oil. The oil in CH$_2$Cl$_2$ (10 ml) was washed with pH 6.5 phosphate buffer, dried and treated with an excess of ethereal hydrogen chloride. The solvent was removed in vacuo and the residue was triturated with ER to give a solid (0.31 g). A portion was crystallised from EA to give the title compound m.p. 109.5°–110.5°.

Analysis. Found: C, 69.5; H, 7.5; N, 2.7. C$_{29}$H$_{37}$NO$_4$.HCl requires C, 69.65; H, 7.65; N, 2.8%.

EXAMPLE 2

(2a) [1α(Z),2β,5β]-(±)-Methyl 6-[[2-[[(1,1'-Biphenyl)-4-yl]methoxy]-5-(1-piperidinyl)cyclopentyl]oxy]-4-hexenoate 3-Carboxypropyltriphenylphosphonium bromide (2.83 g) was added under nitrogen to a stirred solution of potassium-t-butoxide (1.48 g) in dry THF (40 ml).

After 15 min. a solution of Intermediate 5b (865 mg) in dry THF (20 ml) was added dropwise and stirring continued for 1.5 h. Water (7.5 ml) was added and the solvent removed in vacuo. The residue was dissolved in water (75 ml) and washed with ER (2×50 ml). The aqueous layer was adjusted to pH 6.5 with 2N HCl and extracted with $CH_2Cl_2$ (3×50 ml). The combined extracts were dried and evaporated and the residue was dissolved in methanol (25 ml) and treated with conc. $H_2SO_4$ (0.5 ml). After 2 h the solution was neutralised with 8% $NaHCO_3$ solution and extracted with $CH_2Cl_2$ (3×30 ml). The combined extracts were dried and evaporated and the residue was purified by chromatography (A) using 99:1 ER-$Et_3N$ as eluant to give the title compound as an oil (520 mg).

T.l.c. (A) 99:1 ER-$Et_3N$ Rf 0.32.

Analysis. Found: C, 75.5; H, 8.3; N, 2.9. $C_{30}H_{39}NO_4$ requires C, 75.4; H, 8.2; N, 2.9%.

The following compounds were prepared in a similar manner.

(2b) [1α(Z),2α,5β]-(±)-Methyl 6-[[2-[[(1,1'-Biphenyl)-4-yl]methoxy]-5-(1-piperidinyl)cyclopentyl]oxy]-4-hexenoate, from Intermediate 5a. Purification by chromatography (A) using 99:1 EA-$Et_3N$ followed by 95:4:1 EA-methanol-$Et_3N$ as eluants.

T.l.c. (A) 95:4:1 EA-methanol-$Et_3N$ Rf 0.3

Analysis. Found: C, 74.9; H, 8.5; N, 2.9. $C_{30}H_{39}NO_4$ requires C, 75.4; H, 8.2; N, 2.9%.

(2c) [1α(Z),2α,5β]-(±)-Methyl 7-[[2-[[(1,1'-Biphenyl)-4-yl]methoxy]-5-(1-piperidinyl)cyclopentyl]oxy]-5-heptenoate, from Intermediate 5a and 4-carboxybutyltriphenylphosphonium bromide. Purification by chromatography (B) using ER followed by 99:1 ER-methanol as eluants.

T.l.c. (B) ER-eluted twice Rf 0.21

Analysis. Found: C, 75.4; H, 8.6; N, 2.75. $C_{31}H_{41}NO_4$ requires C, 75.7; H, 8.4; N, 2.85%.

(2d) [1α(Z),2α,5β]-(±)-Methyl 8-[[2-[[(1,1'-Biphenyl)-4-yl]methoxy]-5-(1-piperidinyl)cyclopentyl]oxy]-6-octanoate, from Intermediate 5a and 5-carboxypentyltriphenylphosphonium bromide. Purification by chromatography initially on (B) eluting with $CH_2Cl_2$ followed by 49:1 $CH_2Cl_2$-methanol and secondly on (A) eluting with 19:1 EA-methanol followed by 9:1 EA-methanol.

T.l.c. (A) 9:1 EA-methanol Rf 0.13.

I.r. ($CHBr_3$) 1730 $cm^{-1}$.

EXAMPLE 3

[1α(E),2α,5β]-(±)-Methyl 6-[[2-[[2-[[(1,1'-Biphenyl)-4-yl]methoxy]-5-(1-piperidinyl)cyclopentyl]oxy]-4-hexenoate A mixture of p-toluene sulphinic acid (192 mg) and the product of Example 2b (480 mg) in 1,4-dioxan (25 ml) was heated under reflux for 5 days. The solvent was removed in vacuo and the residue in 8% $NaHCO_3$ solution (100 ml) was extracted with $CH_2Cl_2$ (3×50 ml). The combined extracts were dried and evaporated and the residue was purified by chromatography (B) eluting with 19:1 EA-methanol to give the title compound as an oil (260 mg).

T.l.c. (B) 19:1 EA-methanol Rf 0.3

I.r. ($CHBr_3$) 1730, 970 $cm^{-1}$

The compound contained 17% Z-isomer by g.l.c.

EXAMPLE 4

(4a) [1α(Z),2β,5β]-(±)-6-[[2-[[(1,1'-Biphenyl)-4-yl]methoxy]-5-(1-piperidinyl)cyclopentyl]oxy]-4-hexenoic acid, hydrochloride A solution of the product of Example 2a (330 mg) in ethanol (3 ml) was stirred with 5N NaOH (1.5 ml) for 1 h. The solution was diluted with pH 6.5 phosphate buffer (80 ml) and extracted with $CH_2Cl_2$ (3×40 ml). The combined extracts were dried and evaporated and the residue in $CH_2Cl_2$ was treated with an excess of ethereal hydrogen chloride. The solvents were removed in vacuo and the residue was triturated with ER and the resulting solid was crystallised from EA-methanol to give the title compound as a solid (250 mg). m.p. 165°-166°.

Analysis. Found: C, 69.3; H, 7.6; N, 2.6. $C_{29}H_{37}NO_4$.HCl requires C, 69.7; H, 7.7; N, 2.8%.

The following compounds were prepared in a similar manner:

(4b) [1α(E),2α,5β]-(±)-6-[[2-[[(1,1'-Biphenyl)-4-yl]methoxy]-5-(1-piperidinyl)cyclopentyl]oxy]-4-hexenoic acid, hydrochloride, m.p. 146°-150° from the product of Example 3.

I.r. ($CHBr_3$) 1725, 970 $cm^{-1}$.

(4c) [1α(Z),2α,5β]-(±)-7-[[2-[[(1,1'-Biphenyl)-4-yl]methoxy]-5-(1-piperidinyl)cyclopentyl]oxy]-5-heptenoic acid, hydrochloride, m.p. 112°-117° from the product of Example 2c.

I.r. ($CHBr_3$) 1730, 1705 $cm^{-1}$.

(4d) [1α(Z),2α,5β]-(±)-8-[[2-[[(1,1'-Biphenyl)-4-yl]methoxy]-5-(1-piperidinyl)cyclopentyl]oxy]-6-octenoic acid, hydrochloride, m.p. 102°-104° from the product of Example 2d.

I.r. ($CHBr_3$) 1730 $cm^{-1}$

EXAMPLE 5

[1α(E),2α,5β]-(±)-Methyl 6-[[2-[[(1,1'-Biphenyl)-4-yl]methoxy]-5-(1-piperidinyl)cyclopentyl]oxy]-2-hexenoate Carbomethoxymethylenetriphenyl phosphorane (0.4 g) was added under nitrogen to a stirred solution of Intermediate 6 (0.2 g) in dry THF (10 ml). The mixture was heated under reflux for 3 h. The solvent was then removed in vacuo and the residue was purified by chromatography (C) using ER as eluant to give the title compound as an oil (0.113 g).

T.l.c. (C) ER Rf 0.36

Analysis. Found: C, 75.2; H, 8.2; N, 3.1. $C_{30}H_{39}NO_4$ requires C, 75.4; H, 8.2; N, 2.9%.

EXAMPLE 6

[1α(E),2α,5β]-(±)-6-[[2-[[(1,1'-Biphenyl)-4-yl]methoxy]-5-(1-piperidinyl)cyclopentyl]oxy]-2-hexenoic acid, hydrochloride A mixture of tetrbutylammonium hydroxide (0.3 ml, 40% w/v), the product of Example 5 (0.14 g), 2N NaOH solution (6 ml) and THF (6 ml) was vigorously stirred at ambient temperature for 24 h, then adjusted to pH 7 using 2N $H_2SO_4$, diluted with pH 6.5 phosphate buffer (50 ml) and extracted with $CH_2Cl_2$ (3×25 ml). The combined extracts were dried and evaporated and the residue in $CH_2Cl_2$ (2 ml) was treated with an excess of ethereal hydrogen chloride. The solvents were removed in vacuo and the residue was triturated with ER to give a solid which was crystallised from ER to give a solid which was recrystallised from $CH_2Cl_2$-isopropyl acetate to give the title compound (0.103 g) m.p. 155°-156°.

I.r. (CHBr$_3$) 3490, 1720, 1692, 978 cm$^{-1}$.

EXAMPLE 7

(7a) [1R-[1α(Z),2α,5β]]-(±)-6-[[2-[[(1,1'-Biphenyl)-4-yl]methoxy]-5-(1-piperidinyl)cyclopentyl]oxy]-4-hexenoic acid, hydrochloride A solution of Intermediate 9a (415 mg) in ethanol (15 ml) and 2N NaOH (5 ml) was heated under reflux for 2 h. Most of the ethanol was removed in vacuo and the residue in pH 6.5 phosphate buffer (50 ml) was extracted with CH$_2$Cl$_2$ (4×25 ml). The combined extracts were dried and evaporated to low volume and an excess of ethereal hydrogen chloride was added. The solvents were removed in vacuo and the residue was triturated with ER to give the title compound as a solid (353 mg). m.p. 115°-117°.

T.l.c. (B) 1:1 EA-methanol Rf 0.2

[α]$_D^{24.1}$ = +114.2° (CHCl$_3$)

The following compounds were prepared in a similar manner:

(7b) [1S-[1α(Z),2α,5β]]-(−)-6-[[2-[[(1,1'-Biphenyl)-4-yl]methoxy]-5-(1-piperidinyl)cyclopentyl]oxy]-4-hexenoic acid, hydrochloride, m.p. 115°-117° from Intermediate 9b.

[α]$_D^{21.9}$ = −118.3° (CHCl$_3$)

T.l.c. (B) 1:1 EA-methanol Rf 0.2.

(7c) [1α(Z),2α,5β]-(±)-6-[[2-(Phenylmethoxy)-5-(1-piperidinyl)cyclopentyl]oxy]-4-hexenoate, hydrochloride, from Intermediate 9c. The compound was a hygroscopic foam.

T.l.c. (A) 25:15:8:2 EA-isopropanol-H$_2$O-NH$_3$ Rf 0.28

I.r. (Smear) 3420(br.), 1725, 1570 cm$^{-1}$.

(7d) [1α(Z),2α,5β]-(±)-6-[[2-[3-[(1,1'-Biphenyl)-4-yl]propoxy]-5-(1-piperidinyl)cyclopentyl]oxy]-4-hexenoic acid, from Intermediate 9d.

T.l.c (B) EA Rf 0.21

I.r. (CHBr$_3$) 1710, 1595 cm$^{-1}$.

(7e) [1α(Z),2α,5β]-(±)-6-[[2-[[4'-Methoxy-(1,1'-biphenyl)-4-yl]methoxy]-5-(1-piperidinyl)cyclopentyl]oxy]-4-hexenoic acid, from Intermediate 9e.

T.l.c. (A) 25:15:8:2 EA-isopropanol-H$_2$O—NH$_3$ Rf 0.3

I.r. (Smear) 3400(br), 1715, 1610 cm$^{-1}$ (7f) [1α(Z),2α,5β]-(±)-6-[[2-[4-(Phenylmethyl)phenylmethoxy]-5-(1-piperidinyl)cyclopentyl]oxy]-4-hexenoic acid, from Intermediate 9f.

T.l.c. (A) 25:15:8:2 EA-isopropanol-H$_2$O—NH$_3$ Rf 0.43

I.r. (CHBr$_3$) 1705, 1595 cm$^{-1}$ (7g) [1α(Z),2α,5β]-(±)-6-[[2-[(5-Phenyl-3-thienyl)methox]-5-(1-piperidinyl)cyclopentyl]oxy]-4-hexenoic acid, from Intermediate 9g.

T.l.c. (A) 25:15:8:2 EA-isopropanol-H$_2$O—NH$_3$ Rf 0.33

I.r. (CHBr$_3$) 1700-1600 cm$^{-1}$ (7h) [1α(Z),2α,5β]-(±)-6-[[2-[[(1,1'-Biphenyl)-4-yl]methoxy]-5-(4-morpholinyl)cyclopentyl]oxy]-4-hexenoate, from Intermediate 9h.

T.l.c. (A) 25:15:8:2 EA-isopropanol-H$_2$O—NH$_3$ Rf 0.25

I.r. (CHBr$_3$) 1710, 1600 cm$^{-1}$ (7i) [1α(Z),2α,5β]-(±)-6-[[2-[[(1,1'-Biphenyl)-4-yl]methoxy]-5-(hexahydro-1H-azepin-1-yl)cyclopentyl]oxy]-4-hexenoate, hydrochloride, m.p. 127°-129° from Intermediate 9i.

I.r. (CHBr$_3$) 3500, 1720 cm$^{-1}$.

(7j) [1α(Z),2α,5β]-(±)-6-[[2-[[(1,1'-Biphenyl)-4-yl]methoxy]-5-(1-pyrrolidinyl)cyclopentyl]oxy]-4-hexenoic acid, from Intermediate 9j.

T.l.c. (A) 25:15:8:2 EA-isopropanol-H$_2$O—NH$_3$ Rf 0.34

I.r. (CHBr$_3$) 1710, 1595 cm$^{-1}$ (7k) [1α(Z),2α,5β]-(±)-6-[[2-[[(1,1'-Biphenyl)-4-yl]methoxy]-5-(4-thiomorpholinyl)cyclopentyl]oxy]-4-hexenoic acid, from Intermediate 9k.

T.l.c. (A) 25:15:8:2 EA-isopropanol-H$_2$O—NH$_3$ Rf 0.44

I.r. (CHBr$_3$) 1705, 1595 cm$^{-1}$ (7l) (1α,2α,5β)-(±)-6-[[2-[[(1,1'-Biphenyl)-4-yl]methoxy]-5-(1-piperidinyl)cyclopentyl]oxy]hexanoic acid, hydrochloride, m.p. 116°-117° from Intermediate 9l.

T.l.c. (A) 25:15:8:2 EA-isopropanol-H$_2$O—NH$_3$ Rf 0.5

(7m) (1α,2α,5β)-(±)-7-[[2-[[(1,1'-Biphenyl)-4-yl]methoxy]-5-(1-piperidinyl)cyclopentyl]oxy]heptanoic acid, hydrochloride, m.p. 126°-127° from Intermediate 9m.

T.l.c. (A) 25:15:8:2 EA-isopropanol-H$_2$O—NH$_3$ Rf 0.5

(7n) [1α(Z),2β,5β]-(±)-6-[[2-[[(1,1'-Biphenyl)-4-yl]methoxy]-5-(hexahydro-1H-azepin-1-yl)cyclopentyl]oxy]-4-hexenoic acid, hydrochloride, m.p. 70°-71° from Intermediate 9n.

T.l.c. (B) 1:1 EA-methanol Rf 0.37

(7o) [1R-[1α(Z),2β,5β]]-(+)-6-[[2-[[(1,1'-Biphenyl)-4-yl]methoxy]-5-(1-piperidinyl)cyclopentyl]oxy]-4-hexenoic acid, hydrochloride, m.p. 110°-113° from Intermediate 9o.

[α]$_D^{22}$ = +15.8° (CHCl$_3$)

T.l.c. (B) 1:1 EA-methanol Rf 0.28

(7p) [1S-[1α(Z),2β,5β]]-(−)-6-[[2-[[(1,1'-Biphenyl)-4-yl]methoxy]-5-(1-piperidinyl)cyclopentyl]oxy]-4-hexenoic acid, hydrochloride, m.p. 110°-113° from Intermediate 9p.

[α]$_D^{22}$ = −14.8° (CHCl$_3$)

T.l.c. (B) 1:1 EA-methanol Rf 0.28

(7q) [1α(Z),2β,5β]-(±)-6-[[2-[3-(1,1'-Biphenyl)-4-yl]propoxy]-5-(1-piperidinyl)cyclopentyl]oxy]-4-hexenoic acid, from Intermediate 9q.

T.l.c. (B) 1:1 EA-methanol Rf 0.36

I.r. (CHBr$_3$) 1705, 1600 cm$^{-1}$ (7r) [1α(Z),2β,5β]-(±)-6-[[2-[[4'-Methoxy-(1,1'-biphenyl)-4-yl]methoxy]-5-(1-piperidinyl)cyclopentyl]oxy]-4-hexenoic acid, from Intermediate 9r.

T.l.c. (A) 25:15:8:2 EA-isopropanol-H$_2$O—NH$_3$ Rf 0.34

I.r. (CHBr$_3$) 1710. 1610 cm$^{-1}$.

EXAMPLE 8

(1α,2α,5β)-(±)-6-[[2-[[(1,1'-Biphenyl)-4-yl]methoxy]-5-(hexahydro-1H-azepin-1-yl)cyclopentyl]oxy]hexanoic acid, hydrochloride A solution of the product of Example 7i (350 mg) in methanol (25 ml) was hydrogenated over 10% Pd/C (200 mg) at NTP until uptake of hydrogen ceased. The catalyst was removed by filtration and the filtrate was evaporated in vacuo. The residue was triturated with ER to give the title compound as a solid (320 mg) m.p. 168°-170°.

Analysis. Found: C, 69.4; H, 8.4; N, 2.8. C$_{30}$H$_{41}$NO$_4$.HCl requires C, 69.8; H, 8.2; N, 2.7%.

The term "active ingredient" as used below refers to a compound of the invention and may be for example a compound according to one of the previous examples, such as [1R-[1α(Z),2α,5β]]-(+)-6-[[2-[[(1,1'-biphenyl)-4-yl]methoxy]-5-(1-piperidinyl)cyclopentyl]oxy]-4-hexenoic acid.

PHARMACEUTICAL EXAMPLES

TABLETS

These may be prepared by direct compression or wet granulation. The direct compression method is preferred but may not be suitable in all cases as it is dependent upon the dose level and physical characteristics of the active ingredient.

| A. | Direct Compression | mg/tablet |
|---|---|---|
| | Active Ingredient | 100.00 |
| | Microcrystalline Cellulose B.P.C. | 298.00 |
| | Magnesium Stearate | 2.00 |
| | Compression Weight | 400.00 mg |

The active ingredient is sieved through a 250 m$^{-6}$ sieve, blended with the excipients and compressed using 10.0 mm punches. Tablets of other strengths may be prepared by altering the compression weight and using punches to suit.

| B. | Wet Granulation | mg/tablet |
|---|---|---|
| | Active Ingredient | 100.00 |
| | Lactose B.P. | 238.00 |
| | Starch B.P. | 40.00 |
| | Pregelatinised Maize Starch B.P. | 20.00 |
| | Magnesium Stearate B.P. | 2.00 |
| | Compressed Weight | 400.00 mg |

The active ingredient is sieved through a 250 m$^{-6}$ sieve and blended with the lactose, starch and pre-gelatinised starch. The mixed powders are moistened with purified water, granules are made, dried, screened and blended with the magnesium stereate. The lubricated granules are compressed into tablets as described for the direct compression formula.

The tablets may be film coated with suitable film forming materials, e.g. methyl cellulose or hydroxylpropyl methyl cellulose using standard techniques. Alternatively the tablets may be sugar coated.

| Capsules | mg/capsule |
|---|---|
| Ingredient | 100.00 |
| *STA-RX 1500 | 99.00 |
| Magnesium Stearate B.P. | 1.00 |
| Fill Weight | 200.00 mg |

*A form of directly compressible starch supplied by Colorcorn Ltd., Orpington, Kent.

The active ingredient is sieved through a 250 m$^{-6}$ sieve and blended with the other materials. The mix is filled into No. 2 hard gelatin capsules using a suitable filling machine. Other doses may be prepared by altering the fill weight and if necessary changing the capsule size to suit.

| Inhalation cartridges | mg/cartridge |
|---|---|
| Active Ingredient (micronised) | 3.00 |
| Lactose B.P. to | 25.00 |

The active ingredient is micronised in a fluid energy mill to a fine particle size range prior to blending with normal tabletting grade lactose in a high energy mixer. The powder blend is filled into No. 3 hard gelatin capsules on a suitable encapsulating machine. The contents of the cartridge are administered using a powder inhaler.

| Metered Dose Pressurised Aerosol | mg/metered dose | Per Can |
|---|---|---|
| Active Ingredient (micronised) | 0.500 | 120 mg |
| Oleic Acid B.P. | 0.050 | 12 mg |
| Trichlorofluoromethane B.P. | 22.25 | 5.34 g |
| Dichlorodifluoromethane B.P. | 60.90 | 14.62 g |

The active ingredient is micronised in a fluid energy mill to a fine particle size range. The oleic acid is mixed with the trichlorofluoromethane at a temperature of 10°–15° C. and the micronised drug is mixed into this solution with a high shear mixer. The suspension is metered into aluminium aerosol cans and suitable metering valves, delivering a metered dose of 85 mg of suspension, are crimped onto the cans and the dichlorodifluoromethane is pressure filled into the cans through the valves.

| Syrup | mg/5 ml dose |
|---|---|
| Active Ingredient | 100.00 |
| Buffer | |
| Flavour | |
| Colour | as required |
| Preservative | |
| Thickening Agent | |
| Sweetening Agent | |
| Purified Water to | 5.00 ml |

The active ingredient, buffer, flavour, colour, preservative, thickening agent and sweetening agent are dissolved in some of the water, the solution is adjusted to volume and mixed. The syrup produced is clarified by filtration.

Injection for Intravenous Administration

Active Ingredient: 50 mg

Water for injections B.P. to: 5 ml

Sodium chloride or any other suitable material may be added to adjust the tonicity of the solution and the pH may be adjusted to that of maximum stability of the active ingredient using dilute acid or alkali or by the addition of suitable buffer salts. The solution is prepared, clarified and filled into appropriate sized ampoules sealed by fusion of the glass. The injection is sterilised by heating in an autoclave using one of the acceptable cycles. Alternatively the solution may be sterilised by filtration and filled into sterile ampoules under aseptic conditions. The solution may be packed under an inert atmosphere of nitrogen.

| Suspensions | mg/5 ml dose |
|---|---|
| Active ingredient | 100.00 |
| Aluminium monostearate | 75.00 |
| Sweetening agent | |
| Flavour | as required |
| Colour | |

-continued

| Suspensions | mg/5 ml dose |
|---|---|
| Fractionated coconut oil to | 5.00 ml |

The aluminium monostearate is dispensed in about 90% of the fractionated coconut oil. The resulting suspension is heated to 115° C. while stirring and then cooled. The sweetening agent, flavour and colour are added and the active ingredient is suitably dispersed. The suspension is made up to volume with the remaining fractionated coconut oil and mixed.

We claim:

1. Compounds of the formula (1)

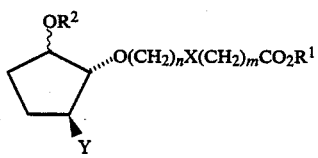

wherein:
$R^1$ is a hydrogen atom or a methyl group;
X is cis or trans —CH=CH— or —CH$_2$CH$_2$—, m is 2, 3 or 4 and n is 1; or X is trans —CH=CH—, m is zero and n is 3;
Y is a saturated heterocyclic amino group attached to the cyclopentane ring via the nitrogen atom, said group being selected from the group consisting of pyrrolidine, piperidine, morpholine, piperazine, thiomorpholine, 1,1-dioxothiomorpholine, homomorpholine and hexamethyleneimino; piperazine substituted at the second nitrogen atom by a methyl, ethyl, butyl, hexyl, benzyl or phenethyl group; and any of said groups substituted on a ring carbon atom by one or more $C_{1-4}$ alkyl groups;
$R^2$ is (i) straight or branched $C_{1-5}$ alkyl substituted by (a) phenyl optionally substituted by $C_{1-6}$ alkyl, $C_{5-7}$ cycloalkyl, phenyl alkyl having a $C_{1-3}$ alkyl portion, thienyl, phenyl (optionally substituted by $C_{1-4}$ alkyl, $C_{1-4}$ alkoxy or phenyl, (b) thionyl optionally substituted by $C_{5-7}$ cycloalkyl or phenyl (optionally substituted by $C_{1-3}$ alkyl, $C_{1-3}$ alkoxy or halogen), or (c) naphthyl (optionally substituted by $C_{1-4}$ alkyl or $C_{1-4}$ alkyl or $C_{1-4}$ alkoxy) or (ii) cinnamyl;
and the physiologically acceptable salts and solvents thereof.

2. Compounds as claimed in claim 1 in which Y is piperidino or hexamethyleneimino.

3. Compounds as claimed in claim 1 in which $R^2$ is benzyl substituted by phenyl or methoxyphenyl, or phenpropyl substituted by phenyl.

4. Compounds as claimed in claim 1 in which n is 1, m is 2 or 4, X is cis —CH=CH— and $R^1$ is a hydrogen atom.

5. Compounds as claimed in claim 1 in which:
$R^1$ is a hydrogen atom;
n is 1, m is 2 and X is cis —CH=CH—;
Y is piperidino or hexamethyleneimino;
$R^2$ is benzyl substituted by phenyl or methoxyphenyl; or phenpropyl substituted by phenyl;
and the physiologically acceptable salts and solvates thereof.

6. Compounds as claimed in claim 1 in which the —OR$^2$ group is in the α-position and the carbon atom carrying the —O(CH$_2$)$_n$X(CH$_2$)$_m$COOR$^1$ group is in the R— configuration.

7. Compounds as claimed in claim 1, said compounds being:
[1R-[1α(Z),2α,5β]]-(+)-6-[[2-[[(1,1'-biphenyl)-4-yl]methoxy]-5-(1-piperidinyl)cyclopentyl]oxy]-4-hexenoic acid or a physiologically acceptable salt or solvate thereof.

8. Compounds as claimed in claim 1, said compounds being:
[1α(Z),2α,5β]-(±)-6-[[2-[[(1,1'-biphenyl)-4-yl]methoxy]-5-(1-piperidinyl)cyclopentyl]oxy]-4-hexenoic acid;
[1α(Z),2α,5β]-(±)-6-[[2-[[(1,1'-biphenyl)-4-yl]methoxy]-5-(hexahydro-1H-azepin-1-yl)cyclopentyl]oxy]-4-hexenoic acid;
[1α(Z),2α,5β]-(±)-6-[[2-[3-[(1,1'-biphenyl)-4-yl]propoxy]-5-(1-piperidinyl)cyclopentyl]oxy]-4-hexenoic acid;
[1α(Z),2β,5β]-(±)-6-[[2-[[4'-methoxy-(1,1'-biphenyl)-4-yl]methoxy]-5-(1-piperidinyl)cyclopentyl]oxy]-4-hexenoic acid; or
[1α(Z),2β,5β]-(±)-6-[[(1,1'-biphenyl)-4-yl]methoxy]-5-(hexahydro-1H-azepin-1-yl)cyclopentyl]oxy]-4-hexenoic acid;
or a physiologically acceptable salt or solvate thereof.

9. A pharmaceutical composition comprising a bronchodilating effective amount of a compound as claimed in claim 1 and a pharmaceutically acceptable carrier.

10. A pharmaceutical composition comprising a vasodilating effective amount of a compound as claimed in claim 1 and a pharmaceutically acceptable carrier.

11. A pharmaceutical composition comprising a blood platelet aggregation inhibiting amount of a compound as claimed in claim 1 and a pharmaceutically acceptable carrier.

* * * * *